(12) United States Patent
Shimizu et al.

(10) Patent No.: US 10,227,494 B2
(45) Date of Patent: Mar. 12, 2019

(54) METALLIC LUSTER PIGMENTS

(71) Applicant: Schlenk Metallic Pigments GmbH, Roth (DE)

(72) Inventors: Kaiman Shimizu, Roth (DE); Fabian Piech, Wendelstein (DE); Adalbert Huber, Bensheim (DE)

(73) Assignee: SCHLENK METALLIC PIGMENTS GMBH, Roth (DE)

( * ) Notice: Subject to any disclaimer, the term of this patent is extended or adjusted under 35 U.S.C. 154(b) by 0 days.

(21) Appl. No.: 14/909,494

(22) PCT Filed: Jul. 29, 2014

(86) PCT No.: PCT/EP2014/002073
§ 371 (c)(1),
(2) Date: Feb. 2, 2016

(87) PCT Pub. No.: WO2015/014484
PCT Pub. Date: Feb. 5, 2015

(65) Prior Publication Data
US 2016/0168387 A1   Jun. 16, 2016

(30) Foreign Application Priority Data

Aug. 2, 2013   (EP) .................. 13003870

(51) Int. Cl.
*C09C 1/40* (2006.01)
*C09C 3/06* (2006.01)
(Continued)

(52) U.S. Cl.
CPC .............. *C09C 1/40* (2013.01); *A61K 8/0266* (2013.01); *A61K 8/19* (2013.01); *A61K 8/25* (2013.01);
(Continued)

(58) Field of Classification Search
CPC ........ A61K 2800/412; A61K 2800/436; A61K 8/0266; A61K 8/19; A61K 8/25;
(Continued)

(56) References Cited

U.S. PATENT DOCUMENTS 4,328,042 A   5/1982   Ostertag et al.
5,277,711 A   1/1994   Schmidt
(Continued)

FOREIGN PATENT DOCUMENTS

CN   101445675 A   6/2009
DE   9400447 U1   8/1994
(Continued)

OTHER PUBLICATIONS

Patent Cooperation Treaty (PCT), International Preliminary Search Report for Application PCT/EP2014/002073 filed Jul. 29, 2014, dated Aug. 11, 2016, International Searching Authority, EP.
(Continued)

*Primary Examiner* — Shuangyi Abu Ali
(74) *Attorney, Agent, or Firm* — McDonald Hopkins LLC

(57) ABSTRACT

The present invention relates to metallic luster pigments, to a process for production thereof and to the use of such metallic luster pigments.

10 Claims, 4 Drawing Sheets

(51) Int. Cl.
  *C09C 1/64* (2006.01)
  *C09D 5/36* (2006.01)
  *C09D 5/38* (2006.01)
  *C09C 1/00* (2006.01)
  *A61K 8/25* (2006.01)
  *A61K 8/26* (2006.01)
  *A61Q 1/02* (2006.01)
  *A61K 8/02* (2006.01)
  *A61K 8/19* (2006.01)
  *C09D 7/62* (2018.01)

(52) U.S. Cl.
  CPC .............. *A61K 8/26* (2013.01); *A61Q 1/02* (2013.01); *C09C 1/0051* (2013.01); *C09C 1/0066* (2013.01); *C09C 1/642* (2013.01); *C09C 3/063* (2013.01); *C09D 5/36* (2013.01); *C09D 5/38* (2013.01); *C09D 7/62* (2018.01); *A61K 2800/412* (2013.01); *A61K 2800/436* (2013.01); *C09C 2200/1054* (2013.01); *C09C 2200/301* (2013.01); *C09C 2200/302* (2013.01); *C09C 2200/303* (2013.01)

(58) Field of Classification Search
  CPC .......... A61K 8/26; A61Q 1/02; C09C 1/0051; C09C 1/0066; C09C 1/40; C09C 1/642; C09C 2200/1054; C09C 2200/301; C09C 2200/302; C09C 2200/303; C09C 3/063; C09D 5/36; C09D 5/38; C09D 7/1225
  See application file for complete search history.

(56) References Cited

U.S. PATENT DOCUMENTS

| | | | |
|---|---|---|---|
| 5,607,504 | A | 3/1997 | Schmid |
| 5,624,486 | A * | 4/1997 | Schmid .................. A61Q 1/02 106/31.65 |
| 5,972,098 | A | 10/1999 | Andes |
| 6,398,999 | B1 | 6/2002 | Josephy |
| 6,599,355 | B1 | 7/2003 | Schmidt et al. |
| 6,776,835 | B2 | 8/2004 | Andes et al. |
| 7,452,597 | B2 | 11/2008 | Bujard |
| 7,943,194 | B2 | 5/2011 | Bujard |
| 8,846,783 | B2 | 9/2014 | Rathschlag |
| 2003/0008120 | A1 | 1/2003 | Andes |
| 2003/0209169 | A1 | 11/2003 | Andes et al. |
| 2004/0244640 | A1 | 12/2004 | Vogt et al. |
| 2005/0013934 | A1 | 1/2005 | Xiong |
| 2005/0223940 | A1 | 10/2005 | Seeger et al. |
| 2007/0104663 | A1 * | 5/2007 | Henglein .............. C09C 1/0015 424/61 |
| 2007/0199478 | A1 | 8/2007 | Schlegl et al. |
| 2010/0047199 | A1 | 2/2010 | Trummer et al. |

FOREIGN PATENT DOCUMENTS

| | | | |
|---|---|---|---|
| DE | 19836810 | A1 | 2/2000 |
| DE | 102007062942 | A1 | 6/2008 |
| EP | 0033457 | B1 | 5/1983 |
| EP | 0806457 | A2 | 11/1997 |
| EP | 1621586 | A1 | 2/2006 |
| JP | H0616965 | | 1/1994 |
| JP | H0693206 | | 4/1994 |
| JP | H08209024 | | 8/1996 |
| JP | H11510552 | | 9/1999 |
| JP | 2002522618 | | 7/2002 |
| JP | 2002528639 | | 9/2002 |
| JP | 2003113330 | | 4/2003 |
| JP | 2006506518 | | 2/2006 |
| JP | 2006527779 | | 12/2006 |
| JP | 2007511655 | | 5/2007 |
| JP | 2008511704 | | 4/2008 |
| JP | 2012513508 | | 6/2012 |
| JP | 2013064053 | | 4/2013 |
| KR | 1020040047972 | | 6/2004 |
| KR | 1020050006248 | | 1/2005 |
| WO | 00/34395 | A1 | 6/2000 |
| WO | 2004/113455 | A2 | 12/2004 |
| WO | 2005/049739 | A2 | 6/2005 |
| WO | 2006/021528 | A2 | 3/2006 |
| WO | 2006/066825 | A2 | 6/2006 |
| WO | 2009/083176 | A1 | 7/2009 |

OTHER PUBLICATIONS

International Search Report and Written Opinion of the International Searching Authority, PCT/EP2014/002073, dated Nov. 19, 2014.
Japan Patent Office, Office action for Japanese Application No. 2016-530381, dated Jul. 4, 2017.
Korean Intellectual Property Office, Decision to Grant a Patent for Korean Application No. 10-2016-7002765, dated Nov. 28, 2018.

* cited by examiner

METALLIC LUSTER PIGMENTS

This application is a 35 U.S.C. 371 national stage filing and claims priority to PCT Application PCT/EP2014/002073 entitled "METALLIC LUSTRE PIGMENTS BASED ON SUBSTRATE FLAKES WITH A THICKNESS OF 1-50 NM," filed Jul. 29, 2014, which claims the benefit of European Application 13003870.6 filed Aug. 2, 2013, each of which are incorporated by reference herein in their entirety.

The present invention relates to metallic luster pigments, to a process for production thereof and to the use of such metallic luster pigments.

Metallic luster pigments or metal effect pigments find wide use in many fields of industry. They are used, for example, for coloring of paints, printing inks, other inks, plastics, glasses, ceramic products and formulations for decorative cosmetics. Of particular economic significance is the use of metallic luster pigments in automotive paint systems. Because of their uncopyable visual effects, they are also used in the production of forgeryproof securities and documents such as banknotes, checks, bank and credit cards, entry tickets and other tickets. They have the particular features of an attractive angle-dependent color appearance (goniochromism) and a metallic luster.

In the case of standard pigments, a color impression arises merely through absorption of particular wavelengths of incident light and scattering reflection. Standard metallic effect pigments reflect the incident light to a high degree and produce a light-dark flop, but no color impression. In the case specific metallic luster pigments, however, optical interference effects give rise to a color impression. Metallic luster pigments of this kind, which are generally based on at least singly coated platelet-shaped substrates, show interference effects as a result of superimposition of various refracted and reflected light rays. White light incident on the flat surface of the coated substrates is partly reflected on the outer surface of the coating. The other portion is refracted and is reflected at interfaces, for example between the coating and substrate surface, and refracted again. The result is therefore superimposition of light rays of different phases. Interference of the reflected light gives rise to a color impression. Because of the dependence of the phase differential on the angle of incidence/observation, the color impression is also angle-dependent. This effect of color change between different reflection angles is referred to as color flop. The phase differential is affected, inter alia, by the thickness of the coating(s), as a result of which the color impression that arises can be adjusted via the coating thickness.

EP-A-0 033 457 describes pigments based on iron oxide-coated aluminum platelets, which have golden to red hues at the specular angle (reflection angle with highest brightness).

DE 94 00 447 U1 describes luster pigments based on nitrated metal (oxide) platelets which have a high hardness and are suitable for use in paints and coatings, in the cosmetics sector and for the coloring of plastics.

WO 2004/113455 describes a method for producing a pigment comprising an $SiO_z$ core material and at least one dielectric layer by microwave deposition of a metal oxide from an aqueous solution.

WO 2005/049739 discloses effect pigments having an aluminum or aluminum alloy core and an aluminum oxide or aluminum oxide/hydroxide-containing layer that encases the aluminum or aluminum alloy core, obtainable by wet-chemical oxidation of aluminum or aluminum alloy pigments in platelet form, wherein the content of metallic aluminum in the aluminum or aluminum alloy core is not more than 90% by weight, based on the total weight of the pigment.

However, the pigments known from the prior art have considerable shortcomings. For instance, the hiding capacity of known pigments is sufficient for certain applications. However, it would be desirable for reasons of efficiency to provide metallic luster pigments having higher hiding capacity. Especially in the case of automotive paint systems, there is a requirement for ever thinner paint layers, which are achievable by means of pigments having higher hiding capacity. Furthermore, metallic luster pigments based on metal oxide-coated aluminum platelets sometimes have disadvantageous safety properties. For instance, pigments of this kind may be inflammable and even be an explosion hazard. Aluminum reacts particularly violently with iron oxide in particular (thermite reaction). These properties of known aluminum-based metallic luster pigments restrict operational safety.

It is thus an object of the present invention to provide an inexpensive metallic luster pigment having a high hiding capacity and a low level of fire characteristics from a performance point of view.

The object is achieved by the embodiments designated in the claims.

More particularly, a metallic luster pigment based on coated aluminum substrate platelets is provided, wherein the aluminum substrate platelets have a thickness of 1 to 50 nm, preferably of 1 to 30 nm, are of monolithic structure and have optionally been passivated and are encased by at least one coating B composed of at least one metal oxide having a high refractive index of at least 1.9, wherein the coating B has a thickness of at least 50 nm, and wherein between the surface of the aluminum substrate platelets and the coating B there is at least one further coating A which encases the substrate platelets and is composed of at least one metal oxide having a low refractive index of at most 1.8, selected from the group consisting of $SiO_2$, $B_2O_3$, $MnO_2$, $MgO$, $GeO_2$ and $Al_2O_3$.

In the context of the present invention, for the sake of simplicity, Si, B and Ge are included among the metals.

The aluminum substrate platelets have an average thickness of at most 50 nm, preferably less than 30 nm, more preferably at most 25 nm, for example at most 20 nm. The average thickness of the aluminum substrate platelets is at least 1 nm, preferably at least 2.5 nm, more preferably at least 5 nm, for example at least 10 nm. Preferred ranges for the thickness of the aluminum substrate platelets are 2.5 to 50 nm, 5 to 50 nm, 10 to 50 nm; 2.5 to 30 nm, 5 to 30 nm, 10 to 30 nm; 2.5 to 25 nm, 5 to 25 nm, 10 to 25 nm, 2.5 to 20 nm, 5 to 20 nm and 10 to 20 nm. Preferably, each substrate platelet has a thickness of maximum homogeneity. As a result of the production, however, variations in thickness may occur within a platelet. These should preferably be not more than ±25%, based on the average thickness of the platelets in question, more preferably at most ±10%, especially preferably at most ±5%. The average thickness is understood here to mean the numerical average of maximum and minimum thickness. The minimum and maximum layer thickness are determined by measurement on the basis of a transmission electron micrograph (TEM) of a (coated) substrate platelet (cf. FIGS. 2 and 3). Since the color of the coated substrate platelets has a linear dependence on the layer thickness, a homogeneous color effect is assured through a precise and homogenized thickness of the uncoated aluminum substrate platelets.

Platelets or flakes are understood in the context of the present invention to mean those having a thickness/length ratio of at least 10:1, preferably higher.

With regard to the variation in layer thickness and the determination of the (average) layer thickness, the above also applies analogously to the thicknesses of the coatings A and B and, if present, C.

Where reference is made here to the "thickness" of a coating or an aluminum substrate platelet, this means the average thickness, unless stated otherwise at the point in question.

The aluminum substrate platelets are of monolithic structure. "Monolithic" in this connection means consisting of a single self-contained unit with no fractures, layering or occlusions, although changes in structure may occur within the substrate platelets (see FIG. 2). The aluminum substrate platelets are preferably of homogeneous structure, meaning that no concentration gradient occurs within the platelets. More particularly, the aluminum substrate platelets do not have a layered structure and do not have any particles distributed therein. More particularly, they do not have a core-shell structure, where the shell consists, for example, of a material suitable for the substrate platelets and the core of another material, for example a silicon oxide. By virtue of their simple structure, the substrate platelets can be produced inexpensively and efficiently. In contrast, a more complex, non-monolithic structure of the substrate platelets results in a more complicated, time-consuming and costly production process.

The proportion by mass of the aluminum substrate platelet in the coated substrate platelet is preferably at most 20% by weight, more preferably at most 15% by weight, for example at most 10% by weight. However, the proportion by mass of the aluminum substrate platelets should not fall below 0.1% by weight, preferably not below 0.5% by weight or 1% by weight.

As a result of the low thickness or the low proportion by mass of the aluminum substrate platelets, the metallic luster pigment of the invention has a particularly high hiding capacity.

The luster pigment of the invention preferably has a total color difference $\Delta E$ of at most 10, more preferably at most 5, especially at most 3. The measurement of $\Delta E$ is effected here to DIN 55987, by application of a paint layer comprising the metallic luster pigment of the invention in a proportion by weight of 18% by weight (dry weight) to a black surface and a white surface. The layer thickness of the dried coat of paint is 15 µm. Thereafter, the total color difference $\Delta E$ between the coats of paint on white and black backgrounds is determined.

In this respect, the present invention, in a further independent embodiment, is also directed to luster pigments having a total color difference $\Delta E$ of at most 10, more preferably at most 5, especially at most 3.

Regardless of the thickness, the size of the uncoated aluminum substrate platelets is not critical and can be matched to the particular end use. In general, the platelets have mean greatest diameters of about 2 to 200 µm, especially about 5 to 100 µm. The d50 of the uncoated aluminum substrate platelets, for use in automotive paints, is preferably 5 to 50 µm, more preferably 10 to 30 µm, but may also assume values of about 70 µm for other uses, for example as industrial paint.

In this document, the d50, unless stated otherwise, is determined with a Sympatec Helos instrument with Quixel wet dispersion. The sample is prepared by pre-dispersing the sample to be analyzed in isopropanol for a period of 3 minutes.

The coated aluminum substrate platelets preferably have a thickness of 70 to 500 nm, more preferably 100 to 400 nm, especially preferably 150 to 320 nm, for example 180 to 290 nm. Because of the low thickness of the substrate platelets, the metallic luster pigment of the invention has a particularly high hiding capacity. The low thickness of the coated aluminum substrate platelets is especially achieved by virtue of the thickness of the uncoated substrate platelets being low, but also by virtue of the thicknesses of the coatings A and, if present, C being adjusted to a minimum value. Since the thickness of coating B determines the color impression of the metallic luster pigment, there is no room for maneuver in this regard in the case of a fixed desired color effect.

It has been assumed to date that exclusively non-transparent (opaque) materials are suitable as substrate platelets. In addition, it has been assumed that uncoated substrate platelets must not go below a certain thickness, in order to avoid (partial) transparency thereof, which would lead, according to this assumption, to a significantly lowered hiding capacity of the resulting luster pigment.

However, it has been found that, surprisingly, it is possible to use (partly or completely transparent) aluminum substrate platelets having a layer thickness of at most 50 nm, preferably at most or less than 30 nm, to produce metallic luster pigments having a much higher hiding capacity than standard metallic luster pigments. The reason for this is probably that the low thickness of the coated aluminum substrate platelets achieves a higher area coverage of the metallic luster pigment. Since the coated substrate platelets are thin, the same mass of pigment can cover a higher area. This advantageous effect more than compensates for the higher transparency of thin, completely or partly transparent substrate platelets, so as ultimately to achieve a higher hiding capacity compared to metallic luster pigments having thick substrate platelets.

Aluminum platelets can be produced, inter alia, by punching out of aluminum foil or by standard grinding and jetting techniques. For example, aluminum platelets are obtainable from the Hall process, a wet grinding process.

The aluminum platelets may take various forms. Substrate platelets used may, for example, be lamellar and lenticular metal platelets or else what are called vacuum metallized pigments (VMP). Lamellar metal platelets feature an irregularly structured edge and, because of their appearance, are also referred to as "cornflakes". Lenticular metal platelets have an essentially regular round edge and, because of their appearance, are also referred to as "silver dollars". Because of their irregular structure, metallic luster pigments based on lamellar metal platelets produce a higher proportion of scattered light than lenticular metal platelets, whereas the proportion of reflective light is predominant in the case of the latter.

The aluminum platelets may be passivated, for example by eloxation (oxide layer) or chromation.

VMPs may be obtained by the release of aluminum from metallized foils. They feature a particularly low thickness of the substrate platelets in the range from 5 to 50 nm, preferably up to or less than 30 nm, and a particularly smooth surface having elevated reflectivity. In the context of the present invention, Al-VMPs are preferred.

The metallic luster pigment of the invention may be a luster pigment either of the leafing type or of the non-leafing type. The metallic luster pigment is preferably a luster pigment of the non-leafing type.

According to the invention, the coated aluminum substrate platelets are encased by at least one coating B of a metal oxide having a high refractive index with a coating thickness of at least 50 nm. Between the coating B and the substrate surface, the coated substrate platelets have at coating A. The substrate platelets may have a further coating C different than the layer B beneath.

In general, coating of part of the surface of the coated substrate platelets is sufficient to obtain a luster pigment. For example, it is possible for only the upper and/or lower side of the platelets to be coated, leaving the side face(s) as they are. According to the invention, however, the entire surface of the optionally passivated substrate platelets, including the side faces, is covered by coating B. The substrate platelets are thus covered completely by coating B. This improves the optical properties of the pigment of the invention and increases the mechanical and chemical durability of the coated substrate platelets. The above also applies to the layer A and preferably also to the layer C, if present.

Even though a plurality of coatings A, B and/or C may be present in each case, the coated substrate platelets preferably each have just one coating A, B and, if present, C.

The coating B is formed from at least one metal oxide of high refractive index. Preferably, the coating B comprises at least 95% by weight, more preferably at least 99% by weight, for example about 100% by weight, of at least one metal oxide of high refractive index.

The coating B has a thickness of at least 50 nm. Preferably, the thickness of coating B is not more than 400 nm, more preferably at most 300 nm.

The ratio of the thickness of coating B to the thickness of the uncoated aluminum substrate platelets is preferably at least 2, for example 4, 8 or 10. In principle, it is not necessary to observe any upper limit for this ratio, but for practical reasons it should be at most 1000, preferably at most 500. The average thickness of a coating or a substrate platelet is determined from the arithmetic mean of the maximum and minimum thickness of the coating/substrate platelet.

Where reference is made here to "substrate platelets" without any distinction as to whether they are coated or not, this refers to uncoated substrate platelets unless stipulated otherwise at the point in question.

According to the invention, between the surface of the aluminum substrate platelets and coating B, there is a further coating A composed of at least one metal oxide having a low refractive index of at most 1.8, selected from the group consisting of $SiO_2$, $B_2O_3$, $MnO_2$, MgO, $GeO_2$ and $Al_2O_3$. Preferably, coating A comprises at least 95% by weight, more preferably at least 99% by weight, for example about 100% by weight, of such a metal oxide of low refractive index Occasionally, the metal oxides which can be used for coatings A, B and C have a certain proportion of secondary constituents and/or impurities. Typical secondary constituents of metal oxides especially include metal hydroxides. For example, a coating of iron oxide may contain a certain proportion of iron hydroxide.

The terms "high refractive index" and "low refractive index" here refer respectively to materials having high and low refractive indices. Materials having a high refractive index have a refractive index of at least 1.9, preferably at least 2.0 and more preferably at least 2.4. Materials of low refractive index have a refractive index of at most 1.8, preferably at most 1.6.

The term "essentially", when applied to a constituent of a composition, means that the composition is formed from the constituent referred to an extent of at least 95% by weight, preferably to an extent of at least 99% by weight, especially preferably to an extent of at least 99% by weight, for example to an extent of about 100% by weight.

Metal oxides of high refractive index that are suitable for coating B are preferably selectively light-absorbing (i.e. colored) metal oxides such as, more particularly, iron(III) oxide (α- and γ-$Fe_2O_3$, red), cobalt(II) oxide (blue), chromium(III) oxide (green), titanium(III) oxide (blue, typically present in a mixture with titanium oxynitrides and titanium nitrides) and vanadium(V) oxide (orange), and mixtures thereof. Also suitable are colorless oxides of high refractive index, such as titanium dioxide and/or zirconium oxide.

Coating B may contain a selectively absorbing dye, preferably 0.001% to 5% by weight, more preferably 0.01% to 1% by weight. Suitable organic and inorganic dyes are those which can be incorporated stably into a metal oxide coating.

Among the metal oxides of low refractive index that are envisaged in accordance with the invention for the coating A, silicon dioxide is preferred. Coating A preferably has a thickness of 1 to 100 nm, more preferably 5 to 50 nm, especially preferably 5 to 20 nm. Preferably, the distance between the surface of the substrate platelets and the inner surface of the coating B is at most 100 nm, more preferably at most 50 nm, especially preferably at most 20 nm. By virtue of the thickness of coating A/the distance between the surface of the substrate platelets and coating B being within the above-specified range, it is possible to ensure that the coated substrate platelets of the metallic luster pigment of the invention have a high hiding capacity and hence a minimum ΔE value.

In a preferred embodiment, the substrate platelets have a further coating C of a metal oxide (hydrate) different than the coating B beneath. Suitable metal oxides are, for example, silicon (di)oxide, silicon oxide hydrate, aluminum oxide, aluminum oxide hydrate, zinc oxide, tin oxide, titanium dioxide, zirconium oxide, iron(III) oxide and chromium(III) oxide. Preference is given to silicon dioxide.

The coating C preferably has a thickness of 10 to 500 nm, more preferably 50 to 300 nm. Through the provision of coating C, for example based on $TiO_2$, it is possible to achieve better interference, while ensuring a high hiding capacity.

In the metallic luster pigment of the invention and the coated substrate platelets, the quantitative ratio α of oxygen not bound to aluminum relative to aluminum is preferably at least 3, more preferably at least 4, especially preferably at least 5. If α is at least 3, this avoids the presence in the coated substrate platelets of a quantitative ratio of oxygen not bound to aluminum relative to aluminum in a stoichiometric ratio of 3/2 (mol/mol). A mixture of aluminum and oxygen compounds, especially $Fe_2O_3$, in which the quantitative ratio α is in the region of 3/2 can react in a highly exothermic manner because of the high oxophilicity of aluminum metal, under some circumstances explosively (aluminothermism, thermite reaction). Therefore, a mixture having α in the region of 3/2 may constitute a safety hazard. However, the reactivity of such a mixture can be lowered by adjusting the ratio α to a value much greater or much smaller than 3/2 (see FIG. 1).

In order to achieve a low value of α, the aluminum content would have to be set at a high level. This would be associated with the disadvantage that the thickness of the substrate platelets of aluminum would have to be set at a high level, the effect of which would be that the hiding capacity of such a luster pigment would be greatly lowered.

Thus, the quantitative ratio α is preferably set to a value above 3/2, namely ≥3. As a result, the coated substrate platelets and the metallic luster pigment of the invention exhibit at least only very low reactivity, if any, with simultaneously high hiding capacity.

The reactivity of the luster pigment is also suppressed or negligibly low when the proportion by mass of iron(III) oxide, if provided as coating B, either alone or in combination with a layer C selected from $TiO_2$, $SnO_2$ and $Al_2O_3$, in the coated substrate platelets is high, preferably at least 65% by weight, more preferably at least 70% by weight, especially preferably at least 75% by weight. However, the content of iron(III) oxide should not be more than 99% by weight, preferably not more than 97% by weight.

In addition, the reactivity of the luster pigment is also suppressed or negligibly low when the content of oxygen not bound to aluminum in the metallic luster pigment is at least 50 mol %, preferably at least 52.5 mol %, more preferably at least 55 mol %, for example at least 57 mol %. However, the quantitative proportion of oxygen not bound to aluminum should not be more than 59 mol %.

In a further independent aspect, the present invention relates to a metallic luster pigment based on coated aluminum substrate platelets, wherein the aluminum platelets are in monolithic form and are encased by at least one coating B of iron(III) oxide which is optionally encased in turn by a layer C selected from $TiO_2$, $SnO_2$ and $Al_2O_3$, especially $TiO_2$, and wherein the proportion by mass of iron(III) oxide in the coated aluminum substrate platelets, either alone or in combination with $TiO_2$, $SnO_2$ or $Al_2O_3$ from layer C, if present, is at least 65% by weight, and between the surface of the aluminum platelets and coating B there is a further coating A of at least one metal oxide having a low refractive index of at most 1.8, selected from the group consisting of $SiO_2$, $B_2O_3$, $MnO_2$, MgO, $GeO_2$ and $Al_2O_3$.

Unless stated otherwise hereinafter, the statements already made above apply to the metallic luster pigment according to this aspect.

A stoichiometric mixture of aluminum and $Fe_2O_3$ (2Al+$Fe_2O_3$→2Fe+$Al_2O_3$) can react in a highly exothermic manner because of the high oxophilicity of aluminum metal, under some circumstances explosively (aluminothermism, thermite reaction). Therefore, such a mixture may constitute a safety hazard. However, the reactivity of a mixture of aluminum and iron(III) oxide can be lowered by adjusting the proportion by mass of iron(III) oxide to a very high or very small value (see FIG. 1).

In this aspect of the invention, the proportion by mass of iron(III) oxide, either alone or in combination with $TiO_2$, $SnO_2$ or $Al_2O_3$ from layer C, if present, is adjusted preferably to a value of ≥65% by weight, based on the total weight of the coated substrate platelets. As a result, the coated substrate platelets or the metallic luster pigment of the invention exhibit(s) at least only very low reactivity, if any.

The proportion by mass of iron(III) oxide in the coated substrate platelets, either alone or in combination with $TiO_2$, $SnO_2$ or $Al_2O_3$ from layer C, if present, is preferably at least 70% by weight, more preferably at least 75% by weight. However, the content of iron(III) oxide should not be more than 99% by weight, preferably not more than 97% by weight.

The reactivity of the coated substrate platelets, in a preferred embodiment of the present invention, is lowered by virtue of the proportion by mass of aluminum metal in the coated substrate platelets being preferably at most 20% by weight, particularly preferably at most 15% by weight, more preferably at most 12% by weight, for example at most 10% by weight. However, the proportion by mass of aluminum metal should not fall below 0.1% by weight, preferably not below 0.5% by weight or 1% by weight.

Elemental aluminum reacts exothermically not just with iron oxide but also with a multitude of other oxygen compounds in which oxygen is not bound to aluminum (aluminothermism). Therefore, in the metallic luster pigment of the invention and the coated aluminum platelets, the quantitative ratio α of oxygen not bound to aluminum relative to aluminum is preferably at least 3, more preferably at least 4, especially preferably at least 5. When α is at least 3 this avoids the presence in the coated aluminum platelets of a quantitative ratio of oxygen not bound to aluminum relative to aluminum in a stoichiometric ratio of 3/2 (mol/mol). A mixture of aluminum and oxygen compounds (for example $Fe_2O_3$) in which the quantitative ratio α is in the region of 3/2 can react in a highly exothermic manner, explosively under some circumstances (aluminothermism). Therefore, a mixture with α in the region of 3/2 may constitute a safety hazard. However, the reactivity of such a mixture can be lowered by adjusting the ratio α to a value much greater or much smaller than 3/2 (see FIG. 1 again).

The quantitative ratio α is preferably adjusted to the above-specified value above 3/2, namely ≥3. As a result, the coated aluminum platelets and the metallic luster pigment of the invention show at least only very low reactivity, if any.

In this aspect of the metallic luster pigment of the invention, no particular demand is made on the thickness of the aluminum platelets, provided that the proportion by mass of iron(III) oxide and preferably also the quantitative ratio α are as specified above. Preferably, the aluminum platelets have a thickness of 1 nm to 20 μm.

In one embodiment, the thickness of the aluminum platelets is preferably in the range from 1 to 50 nm, more preferably 1 to 30 nm, especially preferably 1 to 25 nm. In this case, the thickness of the iron oxide coating is at least 100 nm and is preferably in the range from 100 to 300 nm.

In another embodiment, the thickness of the aluminum platelets is preferably in the range from 100 to 1500 nm. In this case, the coating B preferably has a thickness of 300 to 3500 nm. More preferably, the layer thickness of the coating B is from 400 to 800 nm. If the thickness of the aluminum platelets and coating B is set within this range, it is possible to provide metallic effect pigments having particularly high sparkle.

The process of the invention for producing the metallic luster pigment comprises the steps of providing optionally passivated aluminum substrate platelets, and of coating the aluminum substrate platelets by hydrolytic decomposition of one or more organic metal compounds and/or by precipitation of one or more dissolved metal salts.

To produce coating A, appropriately organic metal compounds (preferably organic silicon compounds) in which the organic radicals are bonded to the metals by oxygen atoms are hydrolyzed in the presence of the substrate platelets and an organic solvent in which the metal compounds are soluble. A multitude of organic solvents are suitable for this purpose, preference being given to isopropanol. In the case of $SiO_2$, the coating A can also be produced in an aqueous medium.

Preferred examples of the organic metal compounds are the acetylacetonates and especially alkoxides, in particular $C_1$-$C_4$-alkoxides, e.g. aluminum triisopropoxide and tetraethoxysilane (tetraethyl orthosilicate, TEOS).

The hydrolysis is preferably conducted in the presence of a base or an acid as catalyst. Suitable bases for the purpose are, for example, not only aqueous alkalis such as sodium hydroxide solution, but especially aqueous ammonia solutions.

Suitable acidic catalysts are, for example, phosphoric acid and organic acids such as acetic acid and oxalic acid.

Water has to be present at least in the amount required in stoichiometric terms for the hydrolysis, but preference is given to 2 to 100 times the amount, especially 5 to 20 times the amount.

Based on the amount of water used, generally 3% to 40% by volume, preferably 5% to 30% by volume, of a 25% by weight aqueous ammonia solution is added.

For the thermal regime, it has been found to be advantageous to heat the reaction mixture to reflux temperature stepwise within 10 to 48 h. When isopropanol is used as solvent, the mixture is stirred, for example, preferably first at 40° C. for 4 to 20 h, then at 60° C. for 4 to 20 h and finally at 80° C. for 2 to 8 h.

In terms of process technology, the coating of substrate platelets with a coating A is appropriately effected as follows:

Aluminum substrate platelets, organic solvent, water and catalyst (acid or preferably base, especially, for example, an aqueous ammonia solution) are initially charged, and then the metal compound to be hydrolyzed is added as a pure substance or in dissolved form, for example as a 30% to 70%, preferably 40% to 60%, by volume solution in the organic solvent. If the metal compound is added in one step, the suspension is then subsequently heated while stirring as described above. Alternatively, the metal compound can be metered in continuously at elevated temperature, in which case water and ammonia may be initially charged or likewise metered in continuously. After the coating has ended, the reaction mixture is cooled back down to room temperature.

In order to prevent agglomerate formation during the coating operation, the suspension can be subjected to significant mechanical stress, such as pumping, vigorous stirring or the action of ultrasound.

Optionally, the coating step can be repeated once or more than once. Should the mother liquor have a milky opaque appearance, it is advisable to exchange it prior to a further coating operation.

The aluminum substrate platelets ensheathed with the coating A can be isolated in a simple manner by filtration, washing with organic solvent, preferably the alcohols used as solvent, and then drying (typically at 20 to 200° C. for 2 to 24 h).

For application of the metal oxide layers (B), it is possible to apply α-iron oxide and chromium oxide layers by hydrolytic decomposition of iron(III) salts such as iron(III) chloride and sulfate or chromium(III) chloride, followed by conversion of the hydroxide-containing layers formed to the oxide layers by heat treatment. The heat treatment is preferably effected at a temperature of 250 to 550° C. for a period of 5 to 60 minutes, preferably 350 to 450° C. for a period of 10 to 30 minutes. It is likewise also possible to achieve a titanium(III) oxide coating by hydrolysis of titanium tetrachloride and subsequent reduction of the titanium dioxide formed with gaseous ammonia.

If a coating C is desired, this can be applied as described for coatings A and B.

With the aid of the production process according to the invention, it is possible to produce the coated substrate platelets reproducibly in large volumes in a simple manner. Fully encased pigment particles having a high quality of the individual coatings (homogeneous, film-like) are obtained.

The present invention further relates, in a further aspect, to the use of the above-described metallic luster pigments for coloring of paints, printing inks, other inks, plastics, glasses, ceramic products and formulations for decorative cosmetics.

The luster pigments of the invention are advantageously suitable for many purposes, such as for coloring of plastics, glasses, ceramic products, formulations for decorative cosmetics, and especially of inks, printing inks and security printing inks, and in particular of paints, for example for the automotive industry.

For these end uses, the pigments of the invention can also advantageously be used in a blend with transparent and hiding white, chromatic and black pigments, and also conventional luster pigments based on metal oxide-coated mica and metal pigments and iron oxides in platelet form.

The metal luster pigments of the invention can be produced inexpensively. They have an exceptionally high hiding capacity and thus offer a variety of advantages for use thereof, for example as a paint in the automobile and motor vehicle industry. The metallic luster pigments according to the present invention additionally have low flammability. They therefore meet strict fire protection regulations and safety requirements.

FIGS. 1 and 2 show results from combustion tests on various coated aluminum platelets having a different proportion by weight of aluminum (FIG. 1) and iron(III) oxide (FIG. 2). The performance rating for the fire characteristics (y axis) as a function of the proportion of aluminum (FIG. 1) or iron(III) oxide (FIG. 2) in the coated substrate platelets is determined by assessing the behavior of the sample in the combustion test described hereinafter.

Figure 1:
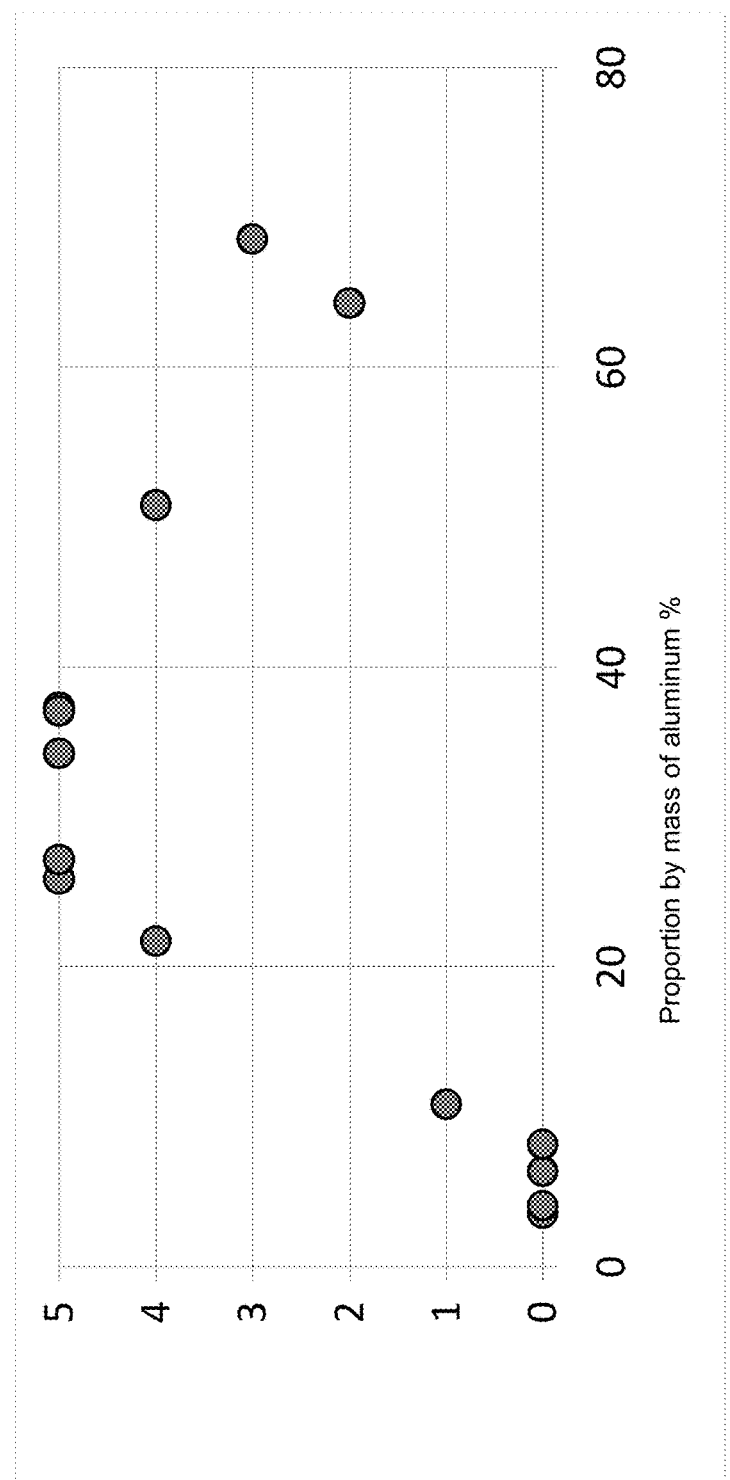

The examples which follow serve to further illustrate the present invention, without being restricted thereto.

EXAMPLE 1 (THIN ALUMINUM PLATELETS WITH THICK IRON OXIDE COATING)

First of all, 50 g of Al platelets (thickness between 20 nm and 30 nm, d50=12 μm) were coated with 10 g of $SiO_2$ by means of a sol-gel method using tetraethyl orthosilicate (TEOS). In a round bottom flask with reflux condenser and stirrer, these Al platelets were admixed with 500 mL of deionized water and heated to 75° C. while stirring. The pH was adjusted to a value of 3.2 by adding a 10% NaOH solution. 1016 g of a 20% $FeCl_3$ solution were added to the reaction mixture, in the course of which the pH was kept essentially constant at 3.2 by simultaneous addition of a 10% NaOH solution. On completion of addition of the $FeCl_3$ solution, the mixture was stirred for a further 15 minutes, in order to assure complete precipitation. The pH was then increased to a value of 7.0 by dropwise addition of a 10% NaOH solution over a period of 30 minutes. After stirring for a further 30 minutes, the coated pigment was separated from the supernatant reaction solution by filtering and washed until it was free of salts. The resultant coated aluminum platelets were dried at 250° C. for 215 minutes and sieved with a sieve (mesh size 25 μm). The resultant product was subjected to an assessment of its color properties and to a fire test as described below.

EXAMPLE 2 (THIN ALUMINUM PLATELETS WITH THIN IRON OXIDE COATING)

In this example, analogously to the method of example 1, coated aluminum platelets were produced, with the difference that, rather than 1016 g, only 102 g of the 20% $FeCl_3$ solution were used. The resultant product was subjected to an assessment of its color properties and to a fire test as described below.

EXAMPLE 3 (THIN ALUMINUM PLATELETS WITH THICK IRON OXIDE COATING AND TITANIUM OXIDE COATING)

This example was conducted analogously to example 1 up to and including the stirring for fifteen minutes after the addition of the $FeCl_3$ solution had ended. Thereafter, the pH was adjusted to 2.0 by adding 10% HCl solution. 412 g of a 30% $TiCl_4$ solution were added to the reaction mixture, in the course of which the pH was kept essentially constant at 2.0 by simultaneously adding a 10% NaOH solution. On completion of addition of the $TiCl_4$ solution, the mixture was stirred for a further 15 minutes, in order to assure complete precipitation. The pH was then increased to a value of 7.0 by dropwise addition of a 10% NaOH solution over a period of 30 minutes. After stirring for a further 30 minutes, the coated pigment was separated from the supernatant reaction solution by filtering and washed until it was free of salts. The resultant coated aluminum platelets were dried at 250° C. and sieved with a sieve (mesh size 25 μm). The resultant product was subjected to an assessment of its color properties and to a fire test as described below.

COMPARATIVE EXAMPLE (THICK ALUMINUM PLATELETS WITH IRON OXIDE COATING)

First of all, 50 g of Al platelets (thickness between 150 nm and 300 nm, d50=18 μm) were coated with 8.8 g of $SiO_2$ by means of a sol-gel method using tetraethyl orthosilicate (TEOS). In a round bottom flask with reflux condenser and stirrer, these Al platelets were admixed with 500 mL of deionized water and heated to 75° C. while stirring. The pH was adjusted to a value of 3.2 by adding a 10% NaOH solution. 660 g of a 20% $FeCl_3$ solution were added to the reaction mixture, in the course of which the pH was kept essentially constant at 3.2 by simultaneously adding a 10% NaOH solution. On completion of addition of the $FeCl_3$ solution, the mixture was stirred for a further 15 minutes in order to assure complete precipitation. The pH was then increased to a value of 7.0 by dropwise addition of a 10% NaOH solution over a period of 30 minutes. After stirring for a further 30 minutes, the coated pigment was separated from the supernatant reaction solution by filtration and washed until it was free of salts. The resultant coated aluminum platelets were dried at 250° C. and sieved with a sieve (mesh size 40 μm). The resultant product was subjected to an assessment of its color properties and to a fire test as described below.

Combustion Test 20 g in each case of the pigments produced were mixed thoroughly with 13.3 g of white spirit. 2 g of this mixture were applied to a glass plate and set on fire. This combustion test is recorded as a video. The fire characteristics are rated on a scale from 0 to 5, 0 meaning that there is merely gentle burnoff of the white spirit without occurrence of any further reaction.

1: isolated sparks during the solvent fire
2: slight evolution of sparks during the solvent fire
3: moderate evolution of sparks during the solvent fire
4: significant evolution of sparks and small explosions or crackling during the solvent fire, glowing of the sample after the solvent has burnt off
5: significant evolution of sparks and explosions or crackling during the solvent fire, and complete conversion of the sample after the solvent has burnt off To measure the total color difference ΔE, a paint layer which comprised the metallic luster pigment of the invention to be examined in a proportion by mass of 18% by weight (dry weight) was applied to a black surface and to a white surface. The layer thickness of the dried coat of paint was 15 μm. Thereafter, the total color difference ΔE between the coats of paint on white and black backgrounds was determined. The results of the measurements are shown in table 1.

Table 1 shows results for various metallic luster pigments. The uncoated substrate platelets consist of aluminum metal. Test numbers 1 to 12 were produced in accordance with the methods from examples 1, 2 and 3 with the necessary modifications for establishment of the individually specific parameters (for example thickness of coatings A, B and, if present, C). Test numbers 5 to 7 and 12 are examples of the present invention; tests 1 to 4 and 8 to 11 are comparative examples. In addition to test numbers 1 to 12, table 1 shows values for the commercially available products Paliochrom L2800 (from BASF) and Meoxal Orange (from Merck) as comparative examples.

It is apparent from table 1 and FIG. 1 that, with a content of aluminum metal in the coated substrate platelets of, in particular, equal to or less than 20% by weight, it is possible to provide a pigment which is noncombustible and is not an explosion hazard. This corresponds to a result of 1 or 0 in the combustion test.

Figure 2:
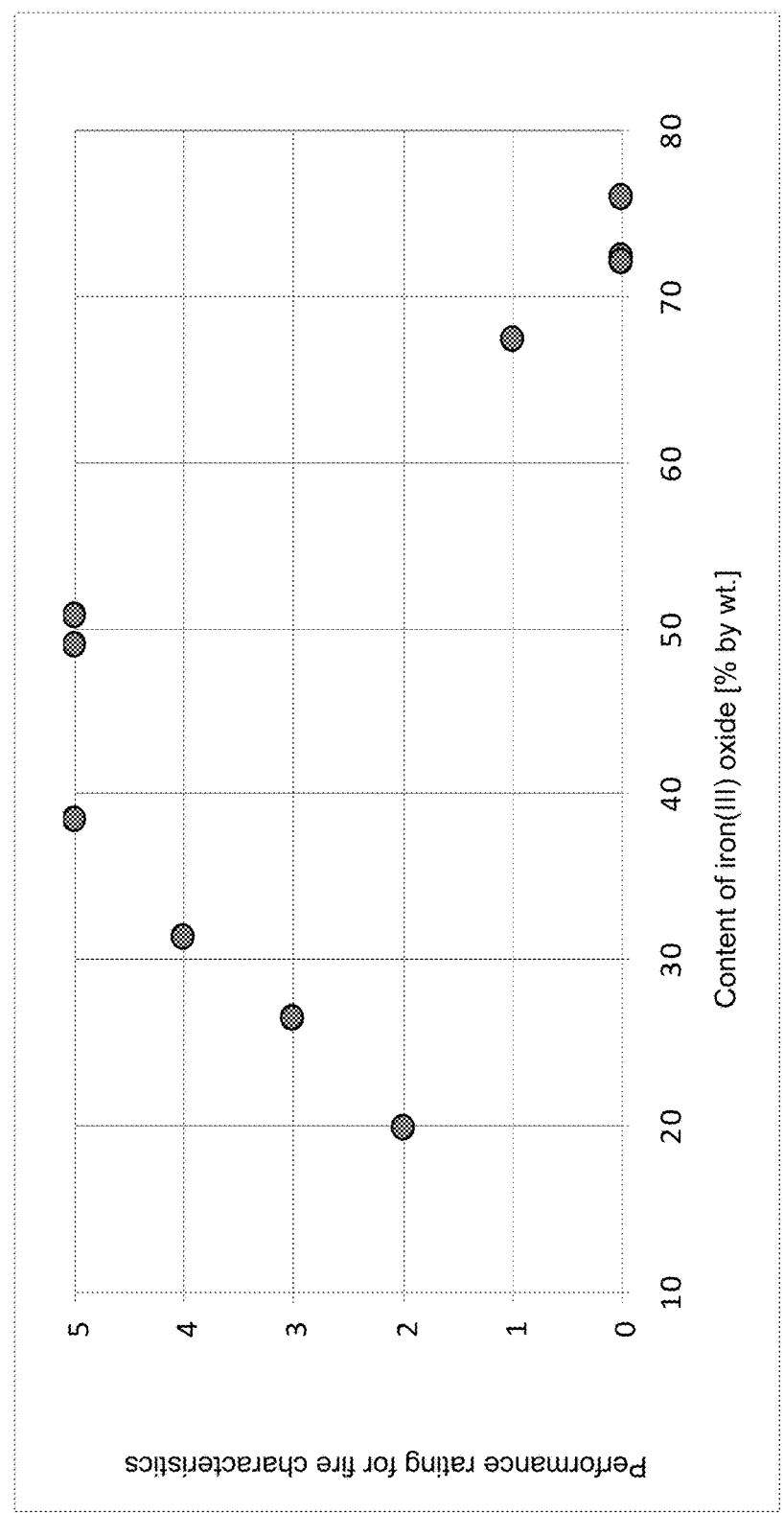
Figure 3:
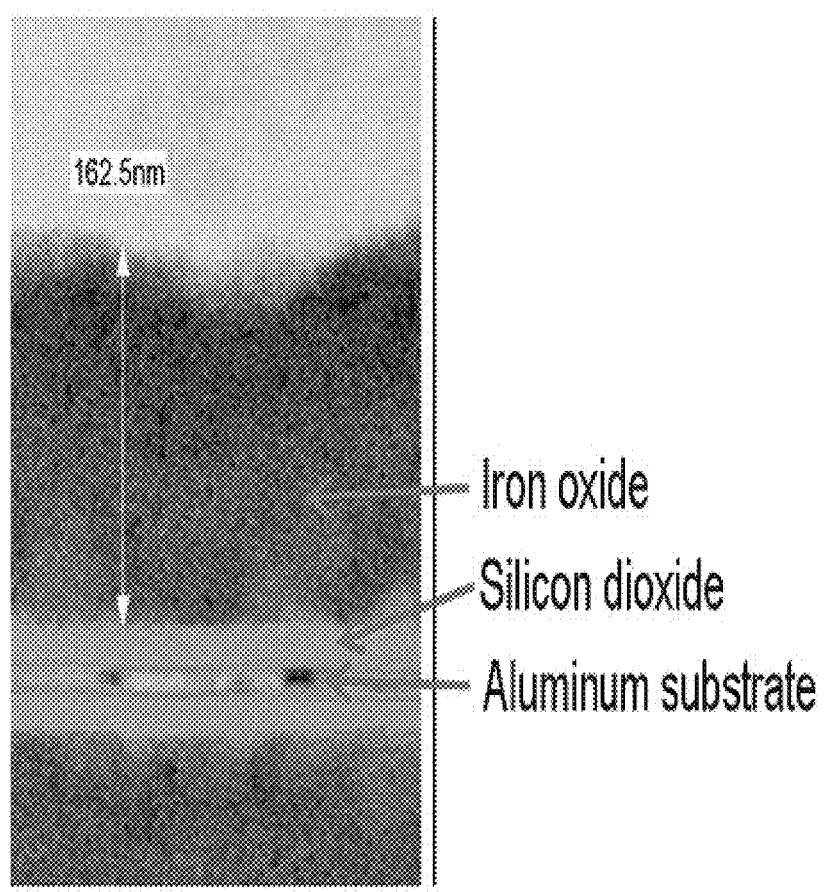
FIG. 3 shows a coated aluminum platelet of the invention. The aluminum platelet has a very homogeneous thickness and is encased by an $SiO_2$ layer (coating A, light) and an iron oxide layer (coating B, dark).
Figure 4:
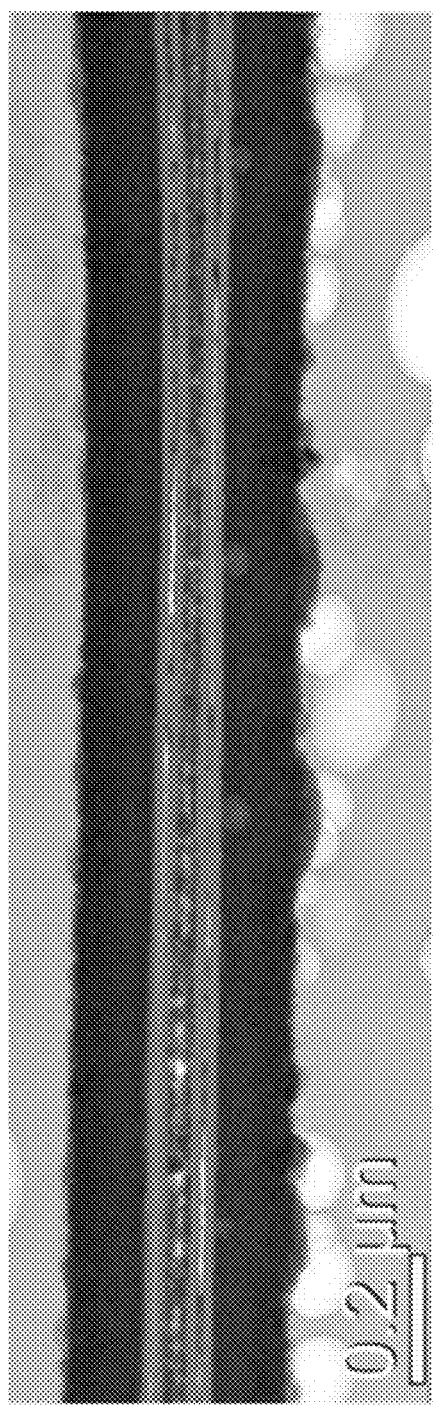
FIG. 4 shows a coated aluminum platelet of the invention having an aluminum core, $SiO_2$ layer (coating A, light) and iron oxide layer (coating B, dark).

It is apparent from table 1 and FIG. 2 that, with an $Fe_2O_3$ content in the coated substrate platelets of, in particular, equal to or greater than 65% by weight, it is possible to provide a pigment which is noncombustible and is not an explosion hazard. This corresponds to a result of 1 or 0 in the combustion test.

In addition, table 1 shows that the metallic luster pigments of the invention have a particularly small color difference ΔE and hence a particularly high hiding capacity. The proportions reported in the table are based on % by weight.

TABLE 1

| No. | Al content | $SiO_2$ content | $Fe_2O_3$ content | $TiO_2$ content | Performance rating for fire characteristics | ΔE | Use of substrate of the invention |
| --- | --- | --- | --- | --- | --- | --- | --- |
| 1 | 37 | 14 | 39 | 0 | 5 | 0.8 | yes |
| 2 | 34 | 21 | 35 | 0 | 5 | 0.6 | yes |
| 3 | 26 | 30 | 30 | 0 | 5 | 0.8 | yes |

TABLE 1-continued

| No. | Al content | $SiO_2$ content | $Fe_2O_3$ content | $TiO_2$ content | Performance rating for fire characteristics | ΔE | Use of substrate of the invention |
|---|---|---|---|---|---|---|---|
| 4 | 22 | 25 | 45 | 0 | 4 | 0.2 | yes |
| 5 | 11 | 13 | 68 | 0 | 1 | 0.7 | yes |
| 6 | 6 | 8 | 73 | 0 | 0 | 0.4 | yes |
| 7 | 4 | 5 | 72 | 0 | 0 | 3.3 | yes |
| 8 | 4 | 6 | 45 | 30 | 0 | 15.4 | yes |
| 9 | 37 | 7 | 49 | 0 | 5 | 0.4 | yes |
| 10 | 51 | 6 | 32 | 0 | 4 | 5.5 | no |
| 11 | 64 | 4 | 20 | 0 | 2 | 11.2 | no |
| 12 | 8 | 3 | 76 | 0 | 0 | 0.8 | yes |
| Paliocrom L2800 | 69 | 1 | 26.6 | nd | 3 | 12.0 | no |
| Meoxal Orange | 27 | 11 | 50.9 | nd | 5 | 25.0 | no |

The invention claimed is:

1. A metallic luster pigment based on coated aluminum substrate platelets,
   wherein the aluminum substrate platelets have a thickness of 5 to 30 nm, are of monolithic structure and have optionally been passivated and are encased by one coating B,
   wherein the coating B has a thickness of at least 50 nm and is formed essentially from iron(III) oxide, and
   wherein between the surface of the aluminum substrate platelets and the coating B there is at least one further coating A which encases the substrate platelets and is composed of at least one metal oxide having a low refractive index of at most 1.8, selected from the group consisting of $SiO_2$, $B_2O_3$, $MnO_2$, MgO, $GeO_2$ and $Al_2O_3$,
   wherein the substrate platelets have a further coating C composed of at least one metal oxide (hydrate) selected from silicon (di)oxide, silicon oxide hydrate, aluminum oxide, aluminum oxide hydrate, zinc oxide, tin oxide, titanium dioxide, zirconium oxide, and chromium(III) oxide.

2. The metallic luster pigment as claimed in claim 1, wherein the coating A is composed of $SiO_2$.

3. The metallic luster pigment as claimed in claim 1, wherein the coating A has a thickness of 1 to 100 nm.

4. The metallic luster pigment as claimed in claim 1, wherein layer A is formed from $SiO_2$ in a thickness of 5 to 50 nm and layer B from $Fe_2O_3$ in a thickness of 50 to 300 nm.

5. A process for producing metallic luster pigments as claimed in claim 1, comprising the steps of:
   providing optionally passivated aluminum substrate platelets,
   coating the aluminum substrate platelets by hydrolytic decomposition of one or more organic metal compounds and/or by precipitation of one or more dissolved metal salts.

6. A composition comprising:
   a metallic luster pigment based on coated aluminum substrate platelets,
   wherein the aluminum substrate platelets have a thickness of 5 to 30 nm, are of monolithic structure and have optionally been passivated and are encased by one coating B,
   wherein the coating B has a thickness of at least 50 nm and is formed essentially from iron(III) oxide and
   wherein between the surface of the aluminum substrate platelets and the coating B there is at least one further coating A which encases the substrate platelets and is composed of at least one metal oxide having a low refractive index of at most 1.8, selected from the group consisting of $SiO_2$, $B_2O_3$, $MnO_2$, MgO, $GeO_2$ and $Al_2O_3$,
   wherein the substrate platelets have a further coating C composed of at least one metal oxide (hydrate) selected from silicon (di)oxide, silicon oxide hydrate, aluminum oxide, aluminum oxide hydrate, zinc oxide, tin oxide, titanium dioxide, zirconium oxide, and chromium(III) oxide.

7. The composition as claimed in claim 6, wherein the coating A is composed of $SiO_2$.

8. The metallic luster pigment as claimed in claim 6, wherein the coating A has a thickness of 1 to 100 nm.

9. The composition as claimed in claim 6, layer A is formed from $SiO_2$ in a thickness of 5 to 50 nm and layer B from $Fe_2O_3$ in a thickness of 50 to 300 nm.

10. The composition of claim 6, wherein the composition is a paint, a printing ink, a plastics, a glass, a ceramic product, or a decorative cosmetic.

* * * * *